US008911689B2

(12) United States Patent
Samper et al.

(10) Patent No.: US 8,911,689 B2
(45) Date of Patent: Dec. 16, 2014

(54) INTERFACING CAPS FOR MICROFLUIDIC DEVICES AND METHODS OF MAKING AND USING THE SAME

(75) Inventors: Victor Donald Samper, Kirchseeon (DE); Christian Rensch, Munich (DE); Christoph Boeld, Munich (DE); Xavier Franci, Loncin (BE)

(73) Assignee: General Electric Company, Niskayuna, NY (US)

( * ) Notice: Subject to any disclaimer, the term of this patent is extended or adjusted under 35 U.S.C. 154(b) by 40 days.

(21) Appl. No.: 13/086,180

(22) Filed: Apr. 13, 2011

(65) Prior Publication Data

US 2012/0027648 A1 Feb. 2, 2012

Related U.S. Application Data

(63) Continuation-in-part of application No. 12/844,385, filed on Jul. 27, 2010.

(51) Int. Cl.

| | |
|---|---|
| ***G01N 33/00*** | (2006.01) |
| ***B01L 3/00*** | (2006.01) |
| ***B65D 51/00*** | (2006.01) |
| *B01F 15/02* | (2006.01) |
| *B01L 9/00* | (2006.01) |
| *B01F 13/00* | (2006.01) |

(52) U.S. Cl.

CPC ..... *B01L 3/50825* (2013.01); *B01L 2300/0672* (2013.01); *B01F 15/0212* (2013.01); *B01L 3/502715* (2013.01); *B01L 9/527* (2013.01); *B01L 2300/161* (2013.01); *B01L 2300/123* (2013.01); *B01F 13/0059* (2013.01); *B01L 2300/0861* (2013.01); *B01L 2200/027* (2013.01); *B65D 51/002* (2013.01); *B01L 3/523* (2013.01); *B01L 3/5635* (2013.01); *B01F 15/0225* (2013.01); *B01L 2300/044* (2013.01); *B01L 2200/0689* (2013.01); *B01L 2300/042* (2013.01)

USPC .......... 422/546; 422/401; 422/68.1; 422/549; 422/550

(58) Field of Classification Search

USPC ......................... 422/401, 68.1, 549, 550, 546

See application file for complete search history.

(56) References Cited

U.S. PATENT DOCUMENTS

| | | | |
|---|---|---|---|
| 4,234,103 | A | 11/1980 | Strobl, Jr. et al. |
| 7,311,882 | B1 | 12/2007 | Renzi |
| 7,435,381 | B2 | 10/2008 | Pugia et al. |

(Continued)

FOREIGN PATENT DOCUMENTS

| | | | |
|---|---|---|---|
| EP | 1909089 | A1 | 4/2008 |
| EP | 1909089 | * | 9/2008 |
| EP | 1995182 | A1 | 11/2008 |
| WO | 2004065288 | A1 | 8/2004 |

OTHER PUBLICATIONS

C.F. Chen et al.; "High-pressure needle interface for thermoplastic microfluidics"; Lab Chip, 2009, 9, 50-55.

Maximilian Focke et al.; "Lab-on-a-Foil: microfluidics on thin and flexible films"; Lab Chip, 2010, 10, 1365-1386.

Jochen Hoffmann et al.; "Pre-storage of liquid reagents in glass ampoules for DNA extraction on a fully integrated lab-on-a-chip cartridge"; First published as an Advance Article on the web Mar. 17, 2010; Lab Chip, 2010, 10, 1480-1484.

(Continued)

*Primary Examiner* — Sam P Siefke

(74) *Attorney, Agent, or Firm* — Seema S. Katragadda

(57) ABSTRACT

An interfacing cap for a reagent storage vessel is provided. The interfacing cap comprises a partitioning element having a structure corresponding to an opening of the reagent storage vessel, a projection fitting disposed on the partitioning element, a holder element, and a puncturing element coupled to the projection fitting.

13 Claims, 3 Drawing Sheets

(56) References Cited

U.S. PATENT DOCUMENTS

| | | | |
|---|---|---|---|
| 7,553,455 | B1 | 6/2009 | Renzi et al. |
| 2003/0099573 | A1 | 5/2003 | Tseung et al. |
| 2005/0014273 | A1 | 1/2005 | Dahm et al. |
| 2008/0273918 | A1 | 11/2008 | Linder et al. |

OTHER PUBLICATIONS

Search Report and Written Opinion from corresponding PCT Application No. PCT/US2012/032865 dated Sep. 19, 2012.

* cited by examiner

INTERFACING CAPS FOR MICROFLUIDIC DEVICES AND METHODS OF MAKING AND USING THE SAME

CROSS-REFERENCE TO RELATED APPLICATION

The present invention is a continuation-in-part of and claims priority to U.S. patent application Ser. No. 12/844,385, filed Jul. 27, 2010.

BACKGROUND

Embodiments of the invention relate to microfluidic devices, and more particularly, to interfacing devices for introducing fluids in the microfluidic devices.

For analytical analysis or preparative steps, reagents are stored in storage containers or vials and need to be transferred to a microfluidic device for carrying out analysis. Conventionally, a reagent storage vial is filled with a reagent volume, and the reagent storage vial is closed using a septum that is disposed on the opening of the reagent storage vial. The septum is held in place using a holder, such as a crimp cap. During analysis or preparation procedures, the septum is punctured and the reagent is transferred in the microfluidic device. The septum may be punctured using a needle at the point of use. The puncturing of the septum makes a fluid and gas seal up to approximately 2 bar over-pressure. Further, puncturing of the septum prior to interfacing the storage container with the microfluidic device results in oozing or spilling of the reagents outside the vial.

Therefore, there exists a need for an interfacing cap for interfacing storage containers with microfluidic devices for preventing or minimizing the leak of reagents of the storage containers during the transfer of the reagent from the storage container to the microfluidic device.

BRIEF DESCRIPTION

In one embodiment, an interfacing cap for a reagent storage vessel is provided. The interfacing cap comprises a partitioning element having a structure corresponding to an opening of the reagent storage vessel, a projection fitting disposed on the partitioning element, a holder element, and a puncturing element coupled to the projection fitting.

In another embodiment, a microfluidic device assembly is provided. The microfluidic device assembly comprises a device substrate comprising a conformal recess; an interfacing cap to interface a reagent storage vessel with the device substrate. The interface cap comprises a partitioning element having a structure corresponding to an opening of the reagent storage vessel, a projection fitting disposed on the partitioning element, a holder element, and a puncturing element coupled to the projection fitting.

In yet another embodiment, a method of making an interfacing cap is provided. The method comprises disposing a partitioning element on an opening of a reagent storage vessel, disposing a projection fitting on the device substrate, disposing at least a portion of the holder element on a portion of the partitioning element and on a portioning of the projection fitting to hold the partitioning element and the projection fitting in place on the reagent storage vessel, and coupling a puncturing element to the projection fitting.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more of the embodiments of the interfacing devices of the invention enable microfluidic devices to efficiently interface with an external fluidic component. In one embodiment, the external fluidic component may be a reagent storage vessel, such as a vial. The reagent storage vessel may be used for introducing or extracting fluids (liquids or gases) from the fluidic devices, such as microfluidic devices.

In certain embodiments, the interfacing cap may comprise a partitioning element configured to be disposed on an opening of a reagent storage vessel, a projection fitting disposed on the partitioning element, a holder element configured to seal the partitioning element between the projection fitting and the vial, and a puncturing element coupled to the projection fitting, wherein the puncturing element is configured to puncture the partitioning element. In certain embodiments, the interfacing cap may be a disposable cap.

The projection fitting of the interfacing cap may be configured to interface the reagent storage vessel with a conformal recess of the microfluidic device. The puncturing element may be at least partially disposed in the projection fitting. The puncturing element is configured to perforate the partitioning element, and form a sealing with the conformal recess. The puncturing element may, for example, be a needle or a section of a capillary tube. The reagent may be transferred from the vessel to the microfluidic device via the puncturing element.

Figure 1:
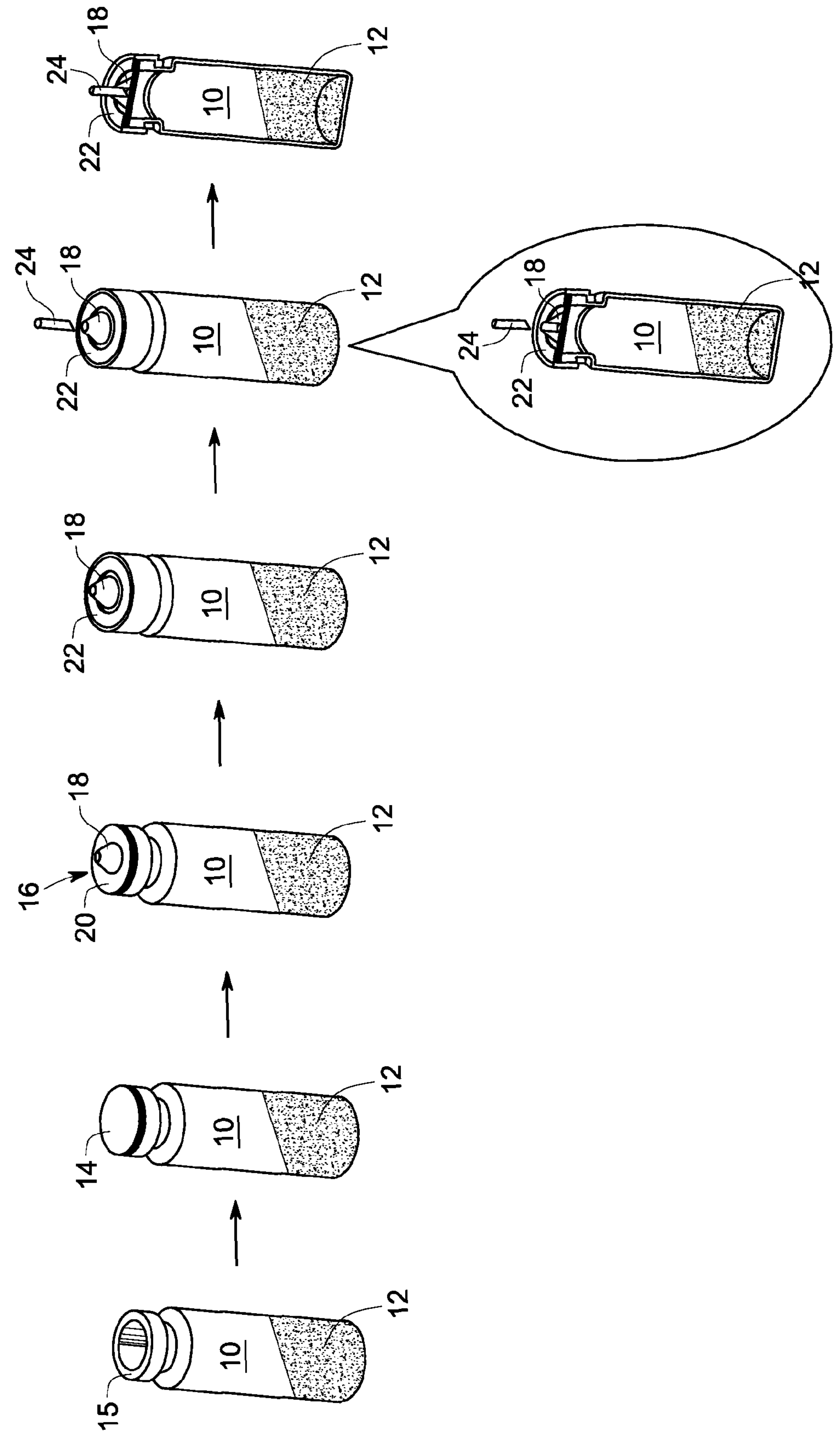
FIG. 1 is a pictorial flow chart of an example of a method of making the interfacing cap.

FIG. 1 illustrates an example of a method of making the interfacing cap of the invention. A reagent storage vessel 10 is filled with the desired reagent 12 under determined environment and atmosphere. A partitioning element 14 may be disposed on an opening 15 of the reagent storage vessel 10. The partitioning element 14 may be made of silicone, polypropylene, polytetrafluoroethylene (TEFLON®), an elastomer, rubber (e.g., natural rubber), or combinations thereof. In one embodiment, the partitioning element 14 may be a re-sealable elastomeric element.

A projection fitting 16 is disposed on the partitioning element 14. The projection fitting 16 may be chosen to resemble the counter cone shape of the conformal recess in which the interfacing cap is to be disposed. In one embodiment, the projection fitting 16 may comprise a tapered geometry. The projection fitting 16 may comprise a cone 18 surrounded by a base 20. At least a portion of the base 20 may be in physical contact with the partitioning element 14. A holder element 22 is used to hold the partitioning element 14 and the projection fitting 16 in place on the vessel 10. In one example, the holder element 22 may be a crimp cap, a screw cap or a glue cap.

The material of the projection fitting 16 may be chosen based on the deformation properties (elastic or plastic deformation) of the material, or values of the temperature and pressure, and type of fluids to which the fluid connector device may be exposed. The materials of the projection fitting 16 and/or a device substrate, of the microfluidic device in which the conformal recess is disposed, are adapted to undergo at least partial deformation. In certain embodiments, the materials of the projection fitting 16 and device substrate may comprise glass, metals, semiconductors, ceramics, polymers, or combinations thereof. The material of the device substrate may be selected to allow one or more conformal recesses to be formed in the coupling substrate. The material of the device substrate may be chosen based on the ease of formation of the desired recess shape in the substrate material. For example, it may be easier to form a conical or a tapered recess in a polymer substrate than in a metal substrate, semiconductor substrate, or ceramic substrate, such as a glass substrate. The polymers for the device substrate and/or the projection fitting 16 may be soft polymers or hard polymers. Soft polymers refer to elastomer type materials such as, but not limited to, polydimethylsiloxane, copolymer of hexafluoropropylene (HFP) and vinylidene fluoride (VDF or $VF_2$), terpolymer of tetrafluoroethylene (TFE), vinylidene fluoride (VDF), and hexafluoropropylene (HFP), perfluoromethylvinylether (PMVE), nitrile rubber, and thermoplastic elastomers such as ELASTRON® and THERMOLAST®. Hard polymers refer to materials such as, but not limited to, polyether ether ketone (PEEK), polypropylene, poly(methyl methacrylate) (PMMA), polyethelene, olefin copolymers (e.g. TOPAS ®), modified ethylene-tetrafluoroethylene) fluoropolymer (ETFE) (e.g. TEFZEL®), polyetherimide (e.g. ULTEM®), cyclic olefin copolymer (COC), and the like.

A portion of a puncturing element 24 may be disposed in the cone 18 of the projection fitting 16. In one embodiment, the puncturing element 24 may be disposed in the cone 18 after disposing the projection fitting 16 on the partitioning element. In this embodiment, the puncturing element 24 may be disposed in the cone 18 either before or after disposing the holder element on the projection fitting 16 and the partitioning element 14. In another embodiment, the puncturing element 24 may be disposed in the cone 18 prior to disposing the projection fitting 16 on the partitioning element 14. In one example, the puncturing element 24 may be coupled to the projection fitting 16 by pressing the puncturing element 24 against the cone 18. The puncturing element 24 may be a needle or a small section of a capillary.

When the vessel 10 having the interfacing cap is pressed against a microfluidic device, the puncturing element 24 may be first pushed backwards into the projection fitting 16 and up to the partitioning element 14, thereby puncturing the partitioning element 14. Upon further pressing of the vessel 10 against the microfluidic device, the puncturing element 24 is sealed to the microfluidic device due to deformation of the material of the conformal recess. The conformal recess or the projection fitting 16, or both may undergo either elastic or plastic deformation to provide a seal between the projection fitting 16 and the device substrate. In one example, only the conformal recess may undergo deformation, for example, an elastic deformation. In another example, both the conformal recess and the projection fitting 16 may undergo deformation. In this example, the conformal recess may undergo elastic deformation, and the reconnectable fit projection fitting 16 may undergo plastic deformation. After formation of the sealing and the puncturing of the partitioning element 14, the vessel 10 is directly coupled to the microfluidic device.

Figure 2:
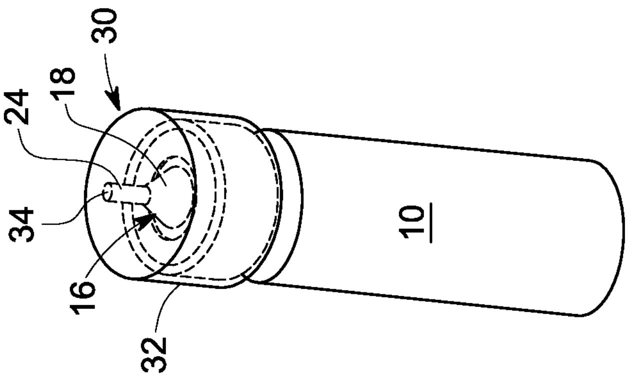
FIG. 2 is a perspective view of an embodiment of a reagent storage vessel comprising an interfacing cap having an sealing element.

FIG. 2 illustrates an interfacing cap 30 comprising a sealing element 32. The sealing element 32 may be disposed either on the interfacing cap 30 or on the microfluidic device (not shown). In embodiments, where the sealing element 32 is disposed on the interfacing cap 30, the sealing element may be disposed around the cone 18 of the projection fitting 16. The sealing element 32 may be disposed on the base 20 of the projection fitting 16. The sealing element 32 may be in the form of an annular cylinder. The height of the cylinder may be smaller or greater than the height of the interfacing cap 30. The sealing element 32 is configured to provide sealing between the conformal recess of the microfluidic device and the interfacing cap 30 even before the interfacing cap 30 during (and after) coupling of the interfacing cap 30 and the conformal recess. Non-limiting examples of the sealing element 32 may include an elastomer. In embodiments where the sealing element 32 is disposed on the microfluidic device, the sealing element may be disposed about the conformal recess in which the interfacing cap is configured to be disposed.

When the reagent needs to be transferred from the vessel 10 to the microfluidic device, the vessel 10 may be disposed on the conformal recess of the microfluidic device. Upon pressing the vessel 10 against the microfluidic device, the sealing element 32 forms an initial soft seal between the vessel 10 and the microfluidic device (not shown) while allowing a first end 34 of the puncturing element 24 to push against the microfluidic device. The reagent storage vessel 10 may be pressed against the microfluidic device, as a result of the force being exerted on the conformal recess (not shown) of the microfluidic device, the first end 34 of the puncturing element 24 forms a sealing with the conformal recess.

After the first end 34 forms the sealing with the puncturing element 24, and upon continued pressing of the , the projection fitting 16 may slide on the puncturing element 24 thereby reducing the distance between the second end (not shown) of the puncturing element 24 and the partitioning element 14. As a result, the puncturing element 24 punctures the partitioning element 14.

In certain embodiments, the sealing element 32 may be an optional element for preventing or minimizing leaks that may otherwise occur upon puncturing of the partitioning element 14 and before sealing of the interfacing cap 30 with the conformal recess of the microfluidic device. For example, the sealing element 32 may not be desired while using a reagent storage vessel with dry reagents. The soft seal may also be optional in embodiments where the system is arranged such that no fluid leaks out of the vessel after puncturing the partitioning element 14. For example, in instances where the fluid in the vessel may not flow out of the vessel upon puncturing of the partitioning element 14 as the flow of the fluid may result in a pressure inside the vessel that is lower than the ambient pressure. In some instances, the ambient pressure may be higher than atmospheric pressure.

Figure 3:
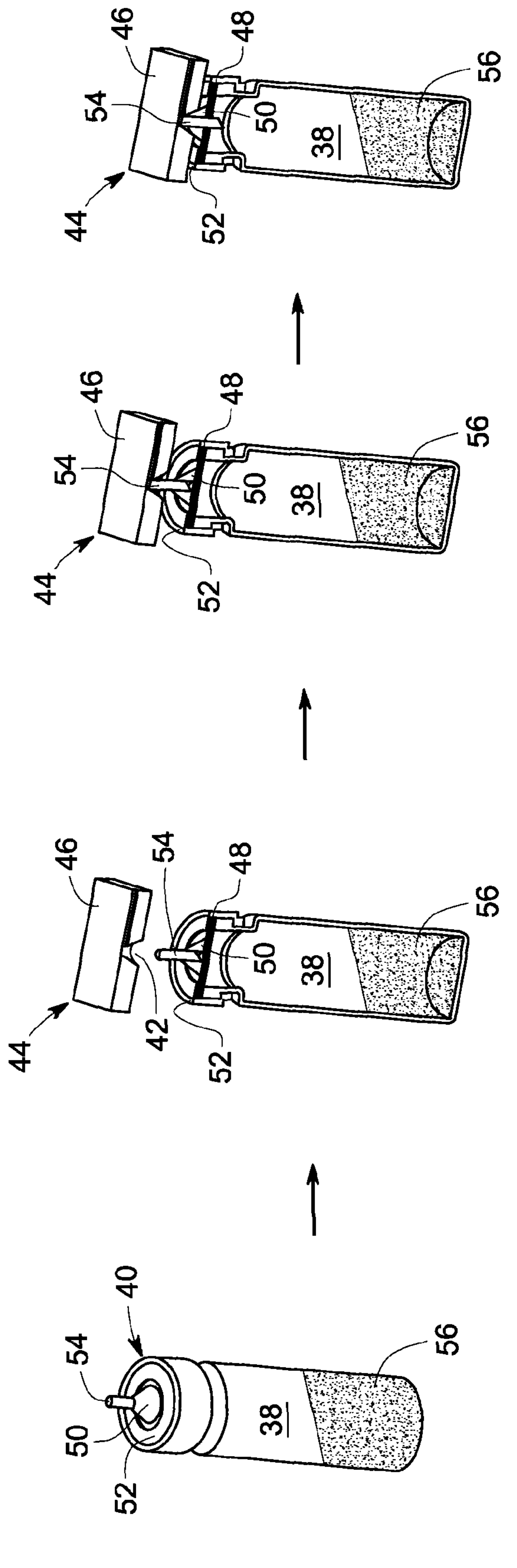
FIG. 3 is an example of a method of making a microfluidic device assembly.

FIG. 3 illustrates the steps in the method of sealing the reagent storage vessel 38 comprising an interfacing cap 40 with a conformal recess 42 of a microfluidic device 44. A microfluidic device substrate 46 comprising a conformal recess 42 is disposed near the reagent storage vessel 38 is such that the conformal recess 42 is aligned with the interfacing cap 40. The interfacing cap 40 comprises a partitioning element 48, a projection fitting 50, a holder component 52, and a puncturing element 54.

In one embodiment, the conformal recess 42 may not be pre-formed in the device substrate 46 prior to receiving the projection fitting 50 of the interfacing cap 40. In this embodiment, the material of the device substrate 46 may be configured to undergo thermal or pressure induced material yielding while receiving the projection fitting 50. That is, when the projection fitting 50 is pressed against the device substrate 46, the yielding of the device substrate 46 in and around the area that receives the projection fitting 50 may form a conformal recess. The conformal recess so formed may have a fluid tight seal with the projection fitting 50. In another embodiment, the material of the projection fitting 50 may be configured to undergo thermal or pressure induced material yielding while being disposed in a conformal recess 42.

Optionally, the conformal recess 42, and/or the tapered geometry of the projection fitting 50 that is configured to be disposed in the conformal recess may include a surface modification. The surface modification may be present either in a portion, or the entire surface of the conformal recess 42 and/or the tapered geometry of the projection fitting 50. In embodiments where the conformal recess is not pre-formed in the coupling substrate, the portion of the coupling substrate that is supposed to undergo deformation upon receiving the projection fitting to form the conformal recess may include surface modification. In one example, the surface modifications may be provided to improve the coupling between the projection fitting and the coupling substrate to reduce or eliminate any leaks. Non-limiting examples of types of surface modifications may include a soft coating, a hard coating, a hydrophobic material, an adhesive, a high roughness surface (such as a plasma etched, or a reactive ion etched surface), a low roughness surface (such as a coated area or polished area), physical features, such as threads. The type of surface modifications may depend on the type of material being employed for the projection fitting and the coupling substrate.

The interfacing cap 40 is disposed on the conformal recess 42, and the vessel 38 is pressed against the microfluidic device 44. The puncturing element 54 is pushed against the partitioning element and punctures the partitioning element 48. Subsequently, the puncturing element 54 forms a sealing with the conformal recess 42. Further compression then results in the projection fitting 50 being disposed in the conical recess 42. At this stage, the vessel 38 is in communication with the microfluidic device 44, and the reagents 56 may be transferred from the vessel 38 to the device 44 with low dead volume arrangement.

Advantageously, the interfacing cap provides a relieable fluid seal and may be configured to reduce the internal dead volume of standard vessels. In addition, the interfacing cap is a low cost device that can be fabricated easily. Also, the interfacing cap may be able to withstand high pressures, while maintaining low dead volume. In one example, the fluid tight seal provided by the interfacing cap may be configured to withstand pressures of over 1000 bars. The fluid connector device may be used with many types of microfluidic devices and with the incorporation of packaging that is easy to design and manufacture. Other advantages include easy installation, quick connection with no tools required, small footprint, leak-tight, and high working pressures.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A microfluidic device assembly, comprising:

a microfluidic device having a device substrate comprising a conformal recess;

a reagent storage vessel comprising an interfacing cap configured to interface the reagent storage vessel with the microfluidic device, and wherein the interfacing cap is configured to provide a fluid tight seal with the microfluidic device, the interfacing cap comprising:

a partitioning element having a structure corresponding to an opening of the reagent storage vessel, wherein the partitioning element is configured to be perforated;

a projection fitting disposed on the partitioning element, wherein the projection fitting is configured to interface the reagent storage vessel with the conformal recess of the device substrate, and wherein at least a portion of the projection fitting is configured to be disposed in the conformal recess of the microfluidic device;

a holder element; and a puncturing element coupled to the projection fitting, wherein the puncturing element is at least partially disposed in the projection fitting, wherein the puncturing element is configured to push into the projection fitting and up to the partitioning element to perforate the partitioning element, and wherein the puncturing element is configured to form a seal with the conformal recess and transfer a reagent from the reagent storage vessel to the microfluidic device.

2. The microfluidic device assembly of claim 1, wherein the puncturing element comprises a needle or a capillary tube.

3. The microfluidic device assembly of claim 1, wherein the puncturing element is configured to form a seal with the conformal recess.

4. The microfluidic device assembly of claim 1, further comprising a sealing element disposed between the reagent storage vessel and the microfluidic device.

5. The microfluidic device assembly of claim 1, wherein the projection fitting resembles a shape counter to a shape of the conformal recess.

6. The microfluidic device assembly of claim 1, wherein the reagent storage vessel comprises dry reagents.

7. The microfluidic device assembly of claim 1, wherein the partitioning element comprises silicone, polypropylene, polytetrafluoroethylene, an elastomer, or combinations thereof.

8. The microfluidic device assembly of claim 1, wherein the projection fitting comprises a metal, a semiconductor, a ceramic, a polymer, or combinations thereof.

9. The microfluidic device assembly of claim 4, wherein the sealing element is annular.

10. The microfluidic device assembly of claim 1, further comprising a sealing element disposed on the interfacing cap, the device substrate, or both.

11. The microfluidic device assembly of claim 1, wherein the holder element comprises a crimp cap, a screw cap or a glue cap.

12. The microfluidic device assembly of claim 1, wherein the projection fitting comprises a cone and a base.

13. The microfluidic device assembly of claim 1, wherein the conformal recess, the projection fitting, or both comprise a surface modification.

* * * * *